United States Patent
Grant et al.

(10) Patent No.: US 8,016,789 B2
(45) Date of Patent: Sep. 13, 2011

(54) PUMP ASSEMBLY WITH A REMOVABLE COVER ASSEMBLY

(75) Inventors: Kevin L. Grant, Litchfield, NH (US); Marc A. Mandro, Bow, NH (US)

(73) Assignee: Deka Products Limited Partnership, Manchester, NH (US)

( * ) Notice: Subject to any disclaimer, the term of this patent is extended or adjusted under 35 U.S.C. 154(b) by 241 days.

(21) Appl. No.: 12/249,496

(22) Filed: Oct. 10, 2008

(65) Prior Publication Data

US 2010/0094215 A1 Apr. 15, 2010

(51) Int. Cl.
*A61M 1/00* (2006.01)
(52) U.S. Cl. .................................... 604/151; 604/114
(58) Field of Classification Search ............... 604/65–67, 604/111, 114, 134–139, 151–155
See application file for complete search history.

(56) References Cited

U.S. PATENT DOCUMENTS

| | | |
|---|---|---|
| 3,631,847 A | 1/1972 | Hobbs, II |
| 3,692,027 A | 9/1972 | Ellinwood, Jr. |
| 3,752,510 A | 8/1973 | Windischman et al. |
| 3,811,121 A | 5/1974 | Heim et al. |
| 3,811,122 A | 5/1974 | Raber et al. |
| 3,837,339 A | 9/1974 | Aisenberg et al. |
| 3,887,393 A | 6/1975 | La Rue, Jr. |
| 3,951,147 A | 4/1976 | Tucker et al. |
| D248,873 S | 8/1978 | Raitto |
| 4,123,631 A | 10/1978 | Lewis |
| 4,146,029 A | 3/1979 | Ellinwood, Jr. |
| 4,150,672 A | 4/1979 | Whitney et al. |
| D254,446 S | 3/1980 | Raitto |
| 4,206,274 A | 6/1980 | Peels |
| 4,215,701 A | 8/1980 | Raitto |
| 4,267,836 A | 5/1981 | Whitney et al. |
| 4,269,908 A | 5/1981 | Stemme |
| 4,270,532 A | 6/1981 | Franetzki et al. |
| 4,273,121 A | 6/1981 | Jassawalla |

(Continued)

FOREIGN PATENT DOCUMENTS

DE 4329229 A1 3/1995

(Continued)

OTHER PUBLICATIONS

International Search Report with Written Opinion, dated Mar. 23, 2010, in international patent application No. PCT/US09/060158, 21 pgs.

(Continued)

*Primary Examiner* — Nicholas D Lucchesi
*Assistant Examiner* — Gerald Landry, II
(74) *Attorney, Agent, or Firm* — McCormick, Paulding & Huber LLP

(57) ABSTRACT

An infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. A combination of the removable cover assembly and at least a portion of the enclosure assembly defines a power supply cavity configured to prevent a removable power supply assembly from being reverse-polarity electrically coupled to the processing logic.

15 Claims, 5 Drawing Sheets

U.S. PATENT DOCUMENTS

| | | |
|---|---|---|
| 4,282,872 A | 8/1981 | Franetzki et al. |
| 4,296,949 A | 10/1981 | Muetterties et al. |
| 4,331,262 A | 5/1982 | Snyder et al. |
| 4,371,594 A | 2/1983 | Ohara et al. |
| 4,373,527 A | 2/1983 | Fischell |
| 4,391,883 A | 7/1983 | Williamson et al. |
| 4,392,847 A | 7/1983 | Whitney et al. |
| 4,392,849 A | 7/1983 | Petre et al. |
| 4,395,259 A | 7/1983 | Prestele et al. |
| 4,437,859 A | 3/1984 | Whitehouse et al. |
| 4,443,218 A | 4/1984 | DeCant, Jr. et al. |
| 4,464,170 A | 8/1984 | Clemens et al. |
| 4,469,481 A | 9/1984 | Kobayashi |
| 4,475,901 A | 10/1984 | Kraegen et al. |
| 4,493,704 A | 1/1985 | Beard et al. |
| 4,494,950 A | 1/1985 | Fischell |
| 4,498,843 A | 2/1985 | Schneider et al. |
| 4,533,346 A | 8/1985 | Cosgrove, Jr. et al. |
| 4,542,532 A | 9/1985 | McQuilkin |
| 4,543,093 A | 9/1985 | Christinger |
| 4,550,731 A | 11/1985 | Batina et al. |
| 4,559,037 A | 12/1985 | Franetzki et al. |
| 4,559,038 A | 12/1985 | Berg et al. |
| 4,562,751 A | 1/1986 | Nason et al. |
| 4,596,575 A | 6/1986 | Rosenberg et al. |
| 4,624,661 A | 11/1986 | Arimond |
| 4,633,878 A | 1/1987 | Bombardieri |
| 4,648,872 A | 3/1987 | Kamen |
| 4,673,396 A | 6/1987 | Urbaniak |
| 4,678,408 A | 7/1987 | Nason et al. |
| 4,685,903 A | 8/1987 | Cable et al. |
| 4,690,878 A | 9/1987 | Nakamura |
| 4,696,671 A | 9/1987 | Epstein et al. |
| 4,731,051 A | 3/1988 | Fischell |
| 4,731,726 A | 3/1988 | Allen, III |
| 4,735,441 A | 4/1988 | Stephens |
| 4,741,731 A | 5/1988 | Starck et al. |
| 4,743,895 A | 5/1988 | Alexander |
| 4,747,828 A | 5/1988 | Tseo |
| 4,790,028 A | 12/1988 | Ramage |
| 4,803,625 A | 2/1989 | Fu et al. |
| 4,804,368 A | 2/1989 | Skakoon et al. |
| 4,809,697 A | 3/1989 | Causey, III et al. |
| 4,826,810 A | 5/1989 | Aoki |
| 4,834,712 A | 5/1989 | Quinn et al. |
| 4,849,852 A | 7/1989 | Mullins |
| 4,856,340 A | 8/1989 | Garrison |
| 4,871,351 A | 10/1989 | Feingold |
| 4,880,712 A | 11/1989 | Gordecki |
| 4,881,063 A | 11/1989 | Fawcett |
| 4,898,578 A | 2/1990 | Rubalcaba, Jr. |
| 4,919,650 A | 4/1990 | Feingold et al. |
| 4,959,640 A | 9/1990 | Hall |
| 4,972,508 A | 11/1990 | King |
| 4,988,337 A | 1/1991 | Ito |
| 4,997,423 A | 3/1991 | Okuda et al. |
| 5,009,646 A | 4/1991 | Sudo et al. |
| 5,019,974 A | 5/1991 | Beckers |
| 5,034,004 A | 7/1991 | Crankshaw |
| 5,049,141 A | 9/1991 | Olive |
| 5,050,612 A | 9/1991 | Matsumura |
| 5,055,830 A | 10/1991 | Cousins et al. |
| 5,063,291 A | 11/1991 | Buehring |
| 5,078,683 A | 1/1992 | Sancoff et al. |
| 5,080,653 A | 1/1992 | Voss et al. |
| 5,088,981 A | 2/1992 | Howson et al. |
| 5,101,814 A | 4/1992 | Palti |
| 5,102,388 A | 4/1992 | Richmond |
| 5,103,216 A | 4/1992 | Sisselman |
| 5,104,374 A | 4/1992 | Bishko et al. |
| 5,150,314 A | 9/1992 | Garratt et al. |
| 5,153,827 A | 10/1992 | Coutré et al. |
| 5,165,407 A | 11/1992 | Wilson et al. |
| 5,174,716 A | 12/1992 | Hora et al. |
| 5,176,502 A | 1/1993 | Sanderson et al. |
| 5,176,644 A | 1/1993 | Srisathapat et al. |
| 5,176,662 A | 1/1993 | Bartholomew et al. |
| 5,181,910 A | 1/1993 | Scanlon |
| 5,187,746 A | 2/1993 | Narisawa |
| 5,191,855 A | 3/1993 | Conforti |
| 5,197,322 A | 3/1993 | Indravudh |
| 5,197,895 A | 3/1993 | Stupecky |
| 5,205,819 A | 4/1993 | Ross et al. |
| 5,216,597 A | 6/1993 | Beckers |
| 5,217,442 A | 6/1993 | Davis |
| 5,248,569 A | 9/1993 | Pine et al. |
| 5,254,093 A | 10/1993 | Bartlett et al. |
| 5,254,096 A | 10/1993 | Rondelet et al. |
| 5,257,971 A | 11/1993 | Lord et al. |
| 5,257,980 A | 11/1993 | Van Antwerp et al. |
| 5,270,702 A | 12/1993 | Krolak |
| 5,290,639 A | 3/1994 | Mallory |
| 5,304,152 A | 4/1994 | Sams |
| 5,307,263 A | 4/1994 | Brown |
| 5,314,416 A | 5/1994 | Lewis et al. |
| 5,317,506 A | 5/1994 | Coutré et al. |
| 5,337,215 A | 8/1994 | Sunderland et al. |
| 5,338,157 A | 8/1994 | Blomquist |
| 5,339,821 A | 8/1994 | Fujimoto |
| 5,341,291 A | 8/1994 | Roizen et al. |
| 5,342,324 A | 8/1994 | Tucker |
| 5,349,852 A | 9/1994 | Kamen et al. |
| 5,350,411 A | 9/1994 | Ryan et al. |
| 5,357,427 A | 10/1994 | Langen et al. |
| 5,364,242 A | 11/1994 | Olsen |
| 5,364,346 A | 11/1994 | Schrezenmeir |
| 5,368,562 A | 11/1994 | Blomquist et al. |
| 5,370,622 A | 12/1994 | Livingston et al. |
| 5,372,133 A | 12/1994 | Hogen Esch |
| 5,376,070 A | 12/1994 | Purvis et al. |
| 5,383,865 A | 1/1995 | Michel |
| 5,389,078 A | 2/1995 | Zalesky et al. |
| 5,390,671 A | 2/1995 | Lord et al. |
| 5,391,157 A | 2/1995 | Harris et al. |
| 5,399,823 A | 3/1995 | McCusker |
| 5,403,648 A | 4/1995 | Chan et al. |
| 5,417,667 A | 5/1995 | Tennican et al. |
| 5,429,602 A | 7/1995 | Hauser |
| 5,433,710 A | 7/1995 | VanAntwerp et al. |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein et al. |
| 5,466,218 A | 11/1995 | Srisathapat et al. |
| 5,472,317 A | 12/1995 | Field et al. |
| 5,476,460 A | 12/1995 | Montalvo |
| 5,478,211 A | 12/1995 | Dominiak et al. |
| 5,482,446 A | 1/1996 | Williamson et al. |
| 5,497,772 A | 3/1996 | Schulman et al. |
| 5,505,709 A | 4/1996 | Funderburk et al. |
| 5,507,727 A | 4/1996 | Crainich |
| 5,508,690 A | 4/1996 | Shur et al. |
| 5,514,097 A | 5/1996 | Knauer |
| 5,514,103 A | 5/1996 | Srisathapat et al. |
| 5,522,803 A | 6/1996 | Teissen-Simony |
| 5,526,844 A | 6/1996 | Kamen et al. |
| 5,527,307 A | 6/1996 | Srisathapat et al. |
| 5,528,359 A | 6/1996 | Taguchi |
| 5,531,697 A | 7/1996 | Olsen et al. |
| 5,531,698 A | 7/1996 | Olsen |
| 5,533,389 A | 7/1996 | Kamen et al. |
| 5,533,996 A | 7/1996 | Murphey et al. |
| 5,538,399 A | 7/1996 | Johnson |
| 5,540,564 A | 7/1996 | Klopfer |
| 5,543,588 A | 8/1996 | Bisset et al. |
| 5,545,140 A | 8/1996 | Conero et al. |
| 5,545,142 A | 8/1996 | Stephens et al. |
| 5,545,143 A | 8/1996 | Fischell |
| 5,545,152 A | 8/1996 | Funderburk et al. |
| 5,558,640 A | 9/1996 | Pfeiler et al. |
| 5,558,641 A | 9/1996 | Glantz et al. |
| 5,562,618 A | 10/1996 | Cai et al. |
| 5,564,915 A | 10/1996 | Johnson |
| 5,567,119 A | 10/1996 | Johnson |
| 5,567,136 A | 10/1996 | Johnson |
| 5,569,026 A | 10/1996 | Novak |
| 5,569,186 A | 10/1996 | Lord et al. |

| | | | | | | |
|---|---|---|---|---|---|---|
| 5,569,187 A | 10/1996 | Kaiser | | 5,885,245 A | 3/1999 | Lynch et al. |
| 5,573,506 A | 11/1996 | Vasko | | 5,897,493 A | 4/1999 | Brown |
| 5,575,310 A | 11/1996 | Kamen et al. | | 5,899,855 A | 5/1999 | Brown |
| 5,582,593 A | 12/1996 | Hultman | | 5,913,310 A | 6/1999 | Brown |
| 5,584,813 A | 12/1996 | Livingston et al. | | 5,918,603 A | 7/1999 | Brown |
| 5,593,390 A | 1/1997 | Castellano et al. | | 5,925,021 A | 7/1999 | Castellano et al. |
| 5,594,638 A | 1/1997 | Iliff | | 5,928,196 A | 7/1999 | Johnson et al. |
| 5,609,060 A | 3/1997 | Dent | | 5,928,202 A | 7/1999 | Linnebjerg |
| 5,609,575 A | 3/1997 | Larson et al. | | 5,931,791 A | 8/1999 | Saltzstein et al. |
| 5,613,945 A | 3/1997 | Cai et al. | | 5,933,136 A | 8/1999 | Brown |
| 5,620,312 A | 4/1997 | Hyman et al. | | 5,935,099 A | 8/1999 | Peterson et al. |
| 5,626,144 A | 5/1997 | Tacklind et al. | | 5,935,105 A | 8/1999 | Manning et al. |
| 5,630,710 A | 5/1997 | Tune et al. | | 5,935,106 A | 8/1999 | Olsen |
| 5,632,729 A | 5/1997 | Cai et al. | | 5,940,801 A | 8/1999 | Brown |
| 5,637,095 A | 6/1997 | Nason et al. | | 5,951,521 A | 9/1999 | Mastrototaro et al. |
| 5,637,420 A | 6/1997 | Jones, Jr. et al. | | 5,954,485 A | 9/1999 | Johnson et al. |
| 5,641,892 A | 6/1997 | Larkins et al. | | 5,954,697 A | 9/1999 | Srisathapat et al. |
| 5,643,212 A | 7/1997 | Coutré et al. | | 5,954,700 A | 9/1999 | Kovelman |
| 5,647,853 A | 7/1997 | Feldmann et al. | | 5,956,501 A | 9/1999 | Brown |
| 5,647,854 A | 7/1997 | Olsen et al. | | 5,957,890 A | 9/1999 | Mann et al. |
| 5,651,775 A | 7/1997 | Walker et al. | | 5,960,403 A | 9/1999 | Brown |
| 5,658,133 A | 8/1997 | Anderson et al. | | 5,968,011 A | 10/1999 | Larsen et al. |
| 5,658,250 A | 8/1997 | Blomquist et al. | | 5,971,963 A | 10/1999 | Choi |
| 5,658,252 A | 8/1997 | Johnson | | 5,973,623 A | 10/1999 | Gupta et al. |
| 5,660,176 A | 8/1997 | Iliff | | 5,980,506 A | 11/1999 | Mathiasen |
| 5,665,065 A | 9/1997 | Colman et al. | | 5,989,216 A | 11/1999 | Johnson et al. |
| 5,669,877 A | 9/1997 | Blomquist | | 5,997,476 A | 12/1999 | Brown |
| 5,669,887 A | 9/1997 | Cooper | | 6,007,941 A | 12/1999 | Hermann et al. |
| 5,678,568 A | 10/1997 | Uchikubo et al. | | 6,009,339 A | 12/1999 | Bentsen et al. |
| 5,681,285 A | 10/1997 | Ford et al. | | 6,014,587 A | 1/2000 | Shaw et al. |
| 5,685,844 A | 11/1997 | Marttila | | 6,017,326 A | 1/2000 | Pasqualucci et al. |
| 5,687,734 A | 11/1997 | Dempsey et al. | | 6,017,328 A | 1/2000 | Fischell et al. |
| 5,695,473 A | 12/1997 | Olsen | | 6,024,539 A | 2/2000 | Blomquist |
| 5,704,366 A | 1/1998 | Tacklind et al. | | 6,032,119 A | 2/2000 | Brown et al. |
| 5,713,856 A | 2/1998 | Eggers et al. | | 6,042,565 A | 3/2000 | Hirschman et al. |
| 5,713,857 A | 2/1998 | Grimard et al. | | 6,056,522 A | 5/2000 | Johnson |
| 5,716,725 A | 2/1998 | Riveron et al. | | 6,056,718 A | 5/2000 | Funderburk et al. |
| 5,718,562 A * | 2/1998 | Lawless et al. ............ 417/1 | | 6,059,753 A | 5/2000 | Faust et al. |
| 5,720,729 A | 2/1998 | Kriesel | | 6,063,059 A | 5/2000 | Kriesel |
| 5,727,241 A | 3/1998 | Yamano et al. | | 6,073,036 A | 6/2000 | Heikkinen et al. |
| 5,733,673 A | 3/1998 | Kunert | | 6,077,055 A | 6/2000 | Vilks |
| 5,743,873 A | 4/1998 | Cai et al. | | 6,086,575 A | 7/2000 | Mejslov |
| 5,752,940 A | 5/1998 | Grimard | | 6,090,081 A | 7/2000 | Sudo et al. |
| 5,755,744 A | 5/1998 | Shaw et al. | | 6,093,172 A | 7/2000 | Funderburk et al. |
| 5,762,632 A | 6/1998 | Whisson | | 6,096,011 A | 8/2000 | Trombley, III et al. |
| 5,764,159 A | 6/1998 | Neftel | | 6,099,507 A | 8/2000 | Heinzerling |
| 5,772,409 A | 6/1998 | Johnson | | 6,101,478 A | 8/2000 | Brown |
| 5,772,635 A | 6/1998 | Dastur et al. | | 6,110,152 A | 8/2000 | Kovelman |
| 5,776,116 A | 7/1998 | Lopez et al. | | 6,112,111 A | 8/2000 | Glantz |
| 5,779,665 A | 7/1998 | Mastrototaro et al. | | 6,123,686 A | 9/2000 | Olsen et al. |
| 5,785,681 A | 7/1998 | Indravudh | | 6,123,690 A | 9/2000 | Mejslov |
| 5,788,669 A | 8/1998 | Peterson | | 6,135,949 A | 10/2000 | Russo et al. |
| 5,788,671 A | 8/1998 | Johnson et al. | | 6,165,154 A | 12/2000 | Gray et al. |
| 5,788,673 A | 8/1998 | Young et al. | | 6,171,287 B1 | 1/2001 | Lynn et al. |
| 5,788,678 A | 8/1998 | Van Antwerp | | 6,202,708 B1 | 3/2001 | Bynum |
| 5,795,337 A | 8/1998 | Grimard | | 6,206,856 B1 | 3/2001 | Mahurkar |
| 5,800,387 A | 9/1998 | Duffy et al. | | 6,211,856 B1 | 4/2001 | Choi et al. |
| 5,800,420 A | 9/1998 | Gross et al. | | 6,216,795 B1 | 4/2001 | Buchl |
| 5,801,600 A | 9/1998 | Butland et al. | | 6,225,711 B1 | 5/2001 | Gupta et al. |
| 5,807,336 A | 9/1998 | Russo et al. | | 6,241,704 B1 | 6/2001 | Peterson et al. |
| 5,810,001 A | 9/1998 | Genga et al. | | 6,246,992 B1 | 6/2001 | Brown |
| 5,810,771 A | 9/1998 | Blomquist | | 6,248,093 B1 | 6/2001 | Moberg |
| 5,814,015 A | 9/1998 | Gargano et al. | | 6,253,804 B1 | 7/2001 | Safabash |
| 5,822,715 A | 10/1998 | Worthington et al. | | 6,254,586 B1 | 7/2001 | Mann et al. |
| 5,823,746 A | 10/1998 | Johnson | | 6,259,587 B1 | 7/2001 | Sheldon et al. |
| 5,832,448 A | 11/1998 | Brown | | 6,267,564 B1 | 7/2001 | Rapheal |
| 5,840,020 A | 11/1998 | Heinonen et al. | | 6,269,340 B1 | 7/2001 | Ford et al. |
| 5,840,026 A | 11/1998 | Uber, III et al. | | 6,270,455 B1 | 8/2001 | Brown |
| 5,843,146 A | 12/1998 | Cross, Jr. | | 6,280,416 B1 | 8/2001 | Van Antwerp et al. |
| 5,851,197 A | 12/1998 | Marano et al. | | 6,283,943 B1 | 9/2001 | Dy et al. |
| 5,851,692 A | 12/1998 | Potts | | 6,293,159 B1 | 9/2001 | Kriesel et al. |
| 5,861,018 A | 1/1999 | Feierbach | | 6,293,925 B1 | 9/2001 | Safabash |
| 5,868,669 A | 2/1999 | Iliff | | 6,305,908 B1 * | 10/2001 | Hermann et al. ............ 417/234 |
| 5,871,465 A | 2/1999 | Vasko | | 6,309,375 B1 | 10/2001 | Glines et al. |
| 5,876,370 A | 3/1999 | Blomquist | | 6,311,868 B1 | 11/2001 | Krietemeier et al. |
| 5,879,143 A | 3/1999 | Cote et al. | | 6,321,158 B1 | 11/2001 | DeLorme et al. |
| 5,879,144 A | 3/1999 | Johnson | | 6,362,591 B1 | 3/2002 | Moberg |
| 5,879,163 A | 3/1999 | Brown et al. | | 6,364,859 B1 | 4/2002 | St. Romain et al. |
| 5,882,256 A | 3/1999 | Shropshire | | 6,364,865 B1 | 4/2002 | Lavi et al. |

| | | |
|---|---|---|
| 6,374,876 B2 | 4/2002 | Bynum |
| 6,375,638 B2 | 4/2002 | Nason et al. |
| 6,416,293 B1 | 7/2002 | Bouchard et al. |
| 6,422,057 B1 | 7/2002 | Anderson |
| 6,423,035 B1 | 7/2002 | Das Kusal et al. |
| 6,427,088 B1 | 7/2002 | Bowman, IV et al. |
| 6,428,509 B1 | 8/2002 | Fielder |
| 6,447,481 B1 | 9/2002 | Duchon et al. |
| 6,453,956 B2 | 9/2002 | Safabash |
| 6,458,102 B1 | 10/2002 | Mann et al. |
| 6,459,424 B1 | 10/2002 | Resman |
| 6,461,329 B1 | 10/2002 | Van Antwerp et al. |
| 6,461,331 B1 | 10/2002 | Van Antwerp |
| 6,466,203 B2 | 10/2002 | Van Ee |
| 6,475,180 B2 | 11/2002 | Peterson et al. |
| 6,475,196 B1 | 11/2002 | Vachon |
| 6,485,461 B1 | 11/2002 | Mason et al. |
| 6,485,465 B2 | 11/2002 | Moberg et al. |
| 6,520,938 B1 | 2/2003 | Funderburk et al. |
| 6,537,268 B1 | 3/2003 | Gibson et al. |
| 6,549,423 B1 | 4/2003 | Brodnick |
| 6,551,276 B1 | 4/2003 | Mann et al. |
| 6,551,277 B1 | 4/2003 | Ford |
| 6,554,798 B1 | 4/2003 | Mann et al. |
| 6,554,800 B1 | 4/2003 | Nezhadian et al. |
| 6,555,986 B2 | 4/2003 | Moberg |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,023 B1 | 5/2003 | Marrs et al. |
| 6,564,105 B2 | 5/2003 | Starkweather et al. |
| 6,571,128 B2 | 5/2003 | Lebel et al. |
| 6,572,542 B1 | 6/2003 | Houben et al. |
| 6,572,586 B1 | 6/2003 | Wojcik |
| 6,577,899 B2 | 6/2003 | Lebel et al. |
| RE38,189 E | 7/2003 | Walker et al. |
| 6,585,644 B2 | 7/2003 | Lebel et al. |
| 6,585,695 B1 | 7/2003 | Adair et al. |
| 6,591,876 B2 | 7/2003 | Safabash |
| 6,592,551 B1 | 7/2003 | Cobb |
| 6,595,756 B2 | 7/2003 | Gray et al. |
| 6,607,509 B2 | 8/2003 | Bobroff et al. |
| 6,613,015 B2 | 9/2003 | Sandstrom et al. |
| D480,477 S | 10/2003 | Bush et al. |
| 6,641,533 B2 | 11/2003 | Causey, III et al. |
| 6,642,936 B1 | 11/2003 | Engholm et al. |
| 6,645,177 B1 | 11/2003 | Shearn |
| 6,648,821 B2 | 11/2003 | Lebel et al. |
| 6,652,493 B1 | 11/2003 | Das |
| 6,652,510 B2 | 11/2003 | Lord et al. |
| 6,656,148 B2 | 12/2003 | Das et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,665,909 B2 | 12/2003 | Collins et al. |
| 6,669,669 B2 | 12/2003 | Flaherty et al. |
| 6,684,058 B1 | 1/2004 | Karacaoglu et al. |
| 6,685,678 B2 | 2/2004 | Evans et al. |
| 6,687,546 B2 | 2/2004 | Lebel et al. |
| 6,689,091 B2 | 2/2004 | Bui et al. |
| 6,691,043 B2 | 2/2004 | Ribeiro, Jr. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,704,034 B1 | 3/2004 | Rodriguez et al. |
| 6,716,195 B2 | 4/2004 | Nolan, Jr. et al. |
| 6,723,072 B2 | 4/2004 | Flaherty et al. |
| 6,733,446 B2 | 5/2004 | Lebel et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,743,205 B2 | 6/2004 | Nolan, Jr. et al. |
| 6,744,350 B2 | 6/2004 | Blomquist |
| 6,749,586 B2 | 6/2004 | Vasko |
| 6,749,587 B2 | 6/2004 | Flaherty |
| 6,752,299 B2 | 6/2004 | Shetler et al. |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,770,067 B2 | 8/2004 | Lorenzen et al. |
| 6,772,650 B2 | 8/2004 | Ohyama et al. |
| 6,800,071 B1 | 10/2004 | McConnell et al. |
| 6,801,420 B2 | 10/2004 | Talbot et al. |
| 6,805,693 B2 | 10/2004 | Gray et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,817,990 B2 | 11/2004 | Yap et al. |
| 6,827,702 B2 | 12/2004 | Lebel et al. |
| 6,830,558 B2 | 12/2004 | Flaherty et al. |
| 6,835,190 B2 | 12/2004 | Nguyen |
| 6,845,465 B2 | 1/2005 | Hashemi |
| 6,852,104 B2 | 2/2005 | Blomquist |
| 6,854,620 B2 | 2/2005 | Ramey |
| 6,872,200 B2 | 3/2005 | Mann et al. |
| 6,873,268 B2 | 3/2005 | Lebel et al. |
| 6,879,930 B2 | 4/2005 | Sinclair et al. |
| 6,902,207 B2 | 6/2005 | Lickliter |
| 6,916,010 B2 | 7/2005 | Beck et al. |
| 6,930,602 B2 | 8/2005 | Villaseca et al. |
| 6,932,584 B2 | 8/2005 | Gray et al. |
| 6,936,029 B2 | 8/2005 | Mann et al. |
| 6,945,760 B2 | 9/2005 | Gray et al. |
| 6,950,708 B2 | 9/2005 | Bowman, IV et al. |
| 6,951,551 B2 | 10/2005 | Hudon |
| 6,958,705 B2 | 10/2005 | Lebel et al. |
| 6,960,192 B1 | 11/2005 | Flaherty et al. |
| 6,960,195 B2 | 11/2005 | Heinz et al. |
| 6,964,643 B2 | 11/2005 | Hovland et al. |
| 6,974,437 B2 | 12/2005 | Lebel et al. |
| 6,978,517 B2 | 12/2005 | Collins et al. |
| 6,979,326 B2 | 12/2005 | Mann et al. |
| 6,994,619 B2 | 2/2006 | Scholten |
| 6,997,905 B2 | 2/2006 | Gillespie, Jr. et al. |
| 6,997,907 B2 | 2/2006 | Safabash et al. |
| 6,997,910 B2 | 2/2006 | Howlett et al. |
| 6,997,920 B2 | 2/2006 | Mann et al. |
| 6,997,921 B2 | 2/2006 | Gray et al. |
| 6,999,854 B2 | 2/2006 | Roth |
| 7,011,608 B2 | 3/2006 | Spencer |
| 7,018,360 B2 | 3/2006 | Flaherty et al. |
| 7,021,560 B2 | 4/2006 | Gray et al. |
| 7,024,245 B2 | 4/2006 | Lebel et al. |
| 7,025,226 B2 | 4/2006 | Ramey |
| 7,025,743 B2 | 4/2006 | Mann et al. |
| 7,029,455 B2 | 4/2006 | Flaherty |
| 7,029,456 B2 | 4/2006 | Ware et al. |
| 7,033,338 B2 | 4/2006 | Vilks et al. |
| 7,033,339 B1 | 4/2006 | Lynn |
| 7,041,082 B2 | 5/2006 | Blomquist et al. |
| 7,045,361 B2 | 5/2006 | Heiss et al. |
| 7,046,230 B2 | 5/2006 | Zadesky et al. |
| 7,050,927 B2 | 5/2006 | Sinclair et al. |
| 7,052,251 B2 | 5/2006 | Nason et al. |
| 7,052,483 B2 | 5/2006 | Wojcik |
| 7,061,140 B2 | 6/2006 | Zhang et al. |
| 7,063,684 B2 | 6/2006 | Moberg |
| 7,066,029 B2 | 6/2006 | Beavis et al. |
| 7,074,209 B2 | 7/2006 | Evans et al. |
| 7,075,512 B1 | 7/2006 | Fabre et al. |
| 7,098,803 B2 | 8/2006 | Mann et al. |
| 7,109,878 B2 | 9/2006 | Mann et al. |
| 7,115,113 B2 | 10/2006 | Evans et al. |
| 7,131,967 B2 | 11/2006 | Gray et al. |
| 7,137,964 B2 | 11/2006 | Flaherty |
| 7,144,384 B2 | 12/2006 | Gorman et al. |
| 7,146,977 B2 | 12/2006 | Beavis et al. |
| 7,278,983 B2 | 10/2007 | Ireland et al. |
| 7,303,549 B2 | 12/2007 | Flaherty et al. |
| 7,305,984 B2 | 12/2007 | Altobelli et al. |
| 7,306,578 B2 | 12/2007 | Gray et al. |
| 7,342,660 B2 | 3/2008 | Altobelli et al. |
| 7,498,563 B2 | 3/2009 | Mandro et al. |
| 7,682,338 B2 | 3/2010 | Griffin |
| 7,927,314 B2 | 4/2011 | Kuracina et al. |
| 2001/0034502 A1 | 10/2001 | Moberg et al. |

| | | |
|---|---|---|
| 2001/0041869 A1 | 11/2001 | Causey, III et al. |
| 2001/0056258 A1 | 12/2001 | Evans |
| 2002/0002326 A1 | 1/2002 | Causey, III et al. |
| 2002/0013613 A1 | 1/2002 | Haller et al. |
| 2002/0022807 A1 | 2/2002 | Duchon et al. |
| 2002/0038392 A1 | 3/2002 | De La Huerga |
| 2002/0043951 A1 * | 4/2002 | Moberg ........................ 318/685 |
| 2002/0052539 A1 | 5/2002 | Haller et al. |
| 2002/0052574 A1 | 5/2002 | Hochman et al. |
| 2002/0056114 A1 | 5/2002 | Fillebrown et al. |
| 2002/0077852 A1 | 6/2002 | Ford et al. |
| 2002/0082665 A1 | 6/2002 | Haller et al. |
| 2002/0091454 A1 | 7/2002 | Vasko |
| 2002/0107481 A1 | 8/2002 | Reilly et al. |
| 2002/0123672 A1 | 9/2002 | Christophersom et al. |
| 2002/0126036 A1 | 9/2002 | Flaherty et al. |
| 2002/0143290 A1 | 10/2002 | Bui et al. |
| 2002/0158838 A1 | 10/2002 | Smith et al. |
| 2002/0169439 A1 | 11/2002 | Flaherty |
| 2002/0173748 A1 | 11/2002 | McConnell et al. |
| 2002/0193679 A1 | 12/2002 | Malave et al. |
| 2002/0193846 A1 | 12/2002 | Pool et al. |
| 2003/0009133 A1 * | 1/2003 | Ramey ........................ 604/155 |
| 2003/0014013 A1 | 1/2003 | Choi |
| 2003/0028079 A1 | 2/2003 | Lebel et al. |
| 2003/0028346 A1 | 2/2003 | Sinclair et al. |
| 2003/0065308 A1 | 4/2003 | Lebel et al. |
| 2003/0076306 A1 | 4/2003 | Zadesky et al. |
| 2003/0088238 A1 | 5/2003 | Poulsen et al. |
| 2003/0114836 A1 | 6/2003 | Estes et al. |
| 2003/0125672 A1 | 7/2003 | Adair et al. |
| 2003/0130618 A1 | 7/2003 | Gray et al. |
| 2003/0132922 A1 | 7/2003 | Philipp |
| 2003/0141981 A1 | 7/2003 | Bui et al. |
| 2003/0161744 A1 | 8/2003 | Vilks et al. |
| 2003/0163089 A1 | 8/2003 | Bynum |
| 2003/0163090 A1 | 8/2003 | Blomquist et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2003/0212379 A1 | 11/2003 | Bylund et al. |
| 2003/0229311 A1 | 12/2003 | Morris et al. |
| 2003/0233069 A1 | 12/2003 | Gillespie, Jr. et al. |
| 2004/0003493 A1 | 1/2004 | Adair et al. |
| 2004/0054326 A1 | 3/2004 | Hommann et al. |
| 2004/0059315 A1 | 3/2004 | Erickson et al. |
| 2004/0064088 A1 | 4/2004 | Gorman et al. |
| 2004/0068230 A1 | 4/2004 | Estes et al. |
| 2004/0073095 A1 | 4/2004 | Causey, III et al. |
| 2004/0073161 A1 | 4/2004 | Tachibana |
| 2004/0082908 A1 | 4/2004 | Whitehurst et al. |
| 2004/0082918 A1 | 4/2004 | Evans et al. |
| 2004/0085215 A1 * | 5/2004 | Moberg et al. ................ 340/679 |
| 2004/0092873 A1 | 5/2004 | Moberg |
| 2004/0116893 A1 | 6/2004 | Spohn et al. |
| 2004/0121767 A1 | 6/2004 | Simpson et al. |
| 2004/0127958 A1 | 7/2004 | Mazar et al. |
| 2004/0133166 A1 | 7/2004 | Moberg et al. |
| 2004/0135078 A1 | 7/2004 | Mandro et al. |
| 2004/0140304 A1 | 7/2004 | Leyendecker |
| 2004/0158193 A1 | 8/2004 | Bui et al. |
| 2004/0162528 A1 | 8/2004 | Horvath et al. |
| 2004/0167464 A1 | 8/2004 | Ireland et al. |
| 2004/0172301 A1 | 9/2004 | Mihai et al. |
| 2004/0176667 A1 | 9/2004 | Mihai et al. |
| 2004/0176725 A1 | 9/2004 | Stutz et al. |
| 2004/0193090 A1 | 9/2004 | Lebel et al. |
| 2004/0207404 A1 | 10/2004 | Zhang et al. |
| 2004/0235446 A1 | 11/2004 | Flaherty et al. |
| 2004/0243065 A1 | 12/2004 | McConnell et al. |
| 2005/0015056 A1 | 1/2005 | Duchon et al. |
| 2005/0021000 A1 | 1/2005 | Adair et al. |
| 2005/0022274 A1 | 1/2005 | Campbell et al. |
| 2005/0027254 A1 | 2/2005 | Vasko |
| 2005/0035956 A1 | 2/2005 | Sinclair et al. |
| 2005/0048900 A1 | 3/2005 | Scholten |
| 2005/0052429 A1 | 3/2005 | Philipp |
| 2005/0055242 A1 | 3/2005 | Bello et al. |
| 2005/0055244 A1 | 3/2005 | Mullan et al. |
| 2005/0062732 A1 | 3/2005 | Sinclair et al. |
| 2005/0063857 A1 | 3/2005 | Alheidt et al. |
| 2005/0065464 A1 | 3/2005 | Talbot et al. |
| 2005/0065817 A1 | 3/2005 | Mihai et al. |
| 2005/0069425 A1 | 3/2005 | Gray et al. |
| 2005/0085760 A1 | 4/2005 | Ware et al. |
| 2005/0096593 A1 | 5/2005 | Pope et al. |
| 2005/0137530 A1 | 6/2005 | Campbell et al. |
| 2005/0137573 A1 | 6/2005 | McLaughlin |
| 2005/0148938 A1 | 7/2005 | Blomquist |
| 2005/0171512 A1 * | 8/2005 | Flaherty ...................... 604/890.1 |
| 2005/0171513 A1 | 8/2005 | Mann et al. |
| 2005/0177111 A1 | 8/2005 | Ozeri et al. |
| 2005/0182366 A1 | 8/2005 | Vogt et al. |
| 2005/0182389 A1 | 8/2005 | LaPorte et al. |
| 2005/0187515 A1 | 8/2005 | Varrichio et al. |
| 2005/0187593 A1 | 8/2005 | Housworth et al. |
| 2005/0192494 A1 | 9/2005 | Ginsberg |
| 2005/0203461 A1 | 9/2005 | Flaherty et al. |
| 2005/0215982 A1 | 9/2005 | Malave et al. |
| 2005/0224705 A1 | 10/2005 | Tobiason et al. |
| 2005/0234404 A1 | 10/2005 | Vilks et al. |
| 2005/0238503 A1 | 10/2005 | Rush et al. |
| 2005/0238507 A1 | 10/2005 | Dilanni et al. |
| 2005/0245904 A1 | 11/2005 | Estes et al. |
| 2005/0250368 A1 | 11/2005 | Singer et al. |
| 2005/0261660 A1 | 11/2005 | Choi |
| 2005/0263615 A1 | 12/2005 | Kriesel et al. |
| 2005/0267363 A1 | 12/2005 | Duchon et al. |
| 2005/0267550 A1 | 12/2005 | Hess et al. |
| 2005/0267928 A1 | 12/2005 | Anderson et al. |
| 2005/0273059 A1 | 12/2005 | Mernoe et al. |
| 2005/0285880 A1 | 12/2005 | Lai et al. |
| 2006/0016800 A1 | 1/2006 | Paradiso et al. |
| 2006/0025663 A1 | 2/2006 | Talbot et al. |
| 2006/0026535 A1 | 2/2006 | Hotelling et al. |
| 2006/0026536 A1 | 2/2006 | Hotelling et al. |
| 2006/0038791 A1 | 2/2006 | Mackey |
| 2006/0041229 A1 | 2/2006 | Garibotto et al. |
| 2006/0065772 A1 | 3/2006 | Grant et al. |
| 2006/0066581 A1 | 3/2006 | Lyon et al. |
| 2006/0097991 A1 | 5/2006 | Hotelling et al. |
| 2006/0100591 A1 | 5/2006 | Alheidt et al. |
| 2006/0106346 A1 | 5/2006 | Sullivan et al. |
| 2006/0123884 A1 | 6/2006 | Selker et al. |
| 2006/0129112 A1 | 6/2006 | Lynn |
| 2006/0144942 A1 | 7/2006 | Evans et al. |
| 2006/0160670 A1 | 7/2006 | Spencer |
| 2006/0161870 A1 | 7/2006 | Hotelling et al. |
| 2006/0161871 A1 | 7/2006 | Hotelling et al. |
| 2006/0173406 A1 | 8/2006 | Hayes et al. |
| 2006/0173444 A1 | 8/2006 | Choy et al. |
| 2006/0178633 A1 | 8/2006 | Garibotto et al. |
| 2006/0178836 A1 | 8/2006 | Bai et al. |
| 2006/0184084 A1 | 8/2006 | Ware et al. |
| 2006/0184123 A1 | 8/2006 | Gillespie, Jr. et al. |
| 2006/0184154 A1 | 8/2006 | Moberg et al. |
| 2006/0200257 A1 | 9/2006 | Kirste et al. |
| 2006/0227117 A1 | 10/2006 | Proctor |
| 2006/0229557 A1 | 10/2006 | Fathallah et al. |
| 2006/0232554 A1 | 10/2006 | Wong et al. |
| 2006/0236262 A1 | 10/2006 | Bathiche et al. |
| 2006/0236263 A1 | 10/2006 | Bathiche et al. |
| 2006/0253085 A1 | 11/2006 | Geismar et al. |
| 2006/0264894 A1 | 11/2006 | Moberg et al. |
| 2006/0282290 A1 | 12/2006 | Flaherty et al. |
| 2007/0049870 A1 | 3/2007 | Gray et al. |
| 2007/0060872 A1 | 3/2007 | Hall et al. |
| 2007/0066956 A1 | 3/2007 | Finkel |
| 2007/0093750 A1 | 4/2007 | Jan et al. |
| 2007/0112298 A1 * | 5/2007 | Mueller et al. .................. 604/65 |
| 2007/0118405 A1 | 5/2007 | Campbell et al. |
| 2007/0161955 A1 | 7/2007 | Bynum et al. |
| 2007/0167905 A1 | 7/2007 | Estes et al. |
| 2007/0178776 A1 * | 8/2007 | Etter et al. ...................... 439/877 |
| 2007/0191770 A1 | 8/2007 | Moberg et al. |
| 2007/0219480 A1 | 9/2007 | Kamen et al. |
| 2007/0219496 A1 | 9/2007 | Kamen et al. |

| | | | |
|---|---|---|---|
| 2007/0219597 A1 | 9/2007 | Kamen et al. | |
| 2007/0228071 A1* | 10/2007 | Kamen et al. | 222/52 |
| 2007/0255250 A1* | 11/2007 | Moberg et al. | 604/503 |
| 2007/0258395 A1* | 11/2007 | Jollota et al. | 370/310 |
| 2008/0009824 A1 | 1/2008 | Moberg et al. | |
| 2008/0051710 A1 | 2/2008 | Moberg et al. | |
| 2008/0051711 A1 | 2/2008 | Mounce et al. | |
| 2008/0097321 A1 | 4/2008 | Mounce et al. | |
| 2008/0097328 A1 | 4/2008 | Moberg et al. | |
| 2008/0125701 A1 | 5/2008 | Moberg et al. | |
| 2008/0160492 A1 | 7/2008 | Campbell et al. | |
| 2008/0161754 A1 | 7/2008 | Marano-Ford | |
| 2008/0177900 A1 | 7/2008 | Grant et al. | |
| 2009/0036870 A1 | 2/2009 | Mounce et al. | |
| 2009/0062767 A1 | 3/2009 | Van Antwerp et al. | |
| 2009/0062778 A1 | 3/2009 | Bengtsson et al. | |
| 2009/0069749 A1 | 3/2009 | Miller et al. | |
| 2009/0099523 A1 | 4/2009 | Grant et al. | |
| 2009/0164251 A1 | 6/2009 | Hayter | |
| 2009/0171291 A1 | 7/2009 | Bente, IV et al. | |
| 2009/0234213 A1 | 9/2009 | Hayes et al. | |
| 2009/0259217 A1 | 10/2009 | Hyde et al. | |
| 2009/0270811 A1 | 10/2009 | Mounce et al. | |

FOREIGN PATENT DOCUMENTS

| | | |
|---|---|---|
| DE | 19627619 A1 | 1/1998 |
| DE | 20110059 A1 | 8/2002 |
| EP | 0256694 A1 | 2/1988 |
| EP | 0258566 A2 | 3/1988 |
| EP | 0338671 A1 | 10/1989 |
| EP | 0398394 A2 | 11/1990 |
| EP | 0554995 B1 | 8/1993 |
| EP | 0749757 A2 | 12/1996 |
| EP | 0763368 A2 | 3/1997 |
| EP | 0806738 A1 | 11/1997 |
| EP | 0830597 B1 | 3/1998 |
| EP | 1007137 B1 | 6/2000 |
| EP | 1109586 B1 | 6/2001 |
| EP | 1177802 A1 | 2/2002 |
| EP | 1338295 A1 | 8/2003 |
| EP | 1473050 A1 | 3/2004 |
| EP | 1115435 B1 | 8/2005 |
| EP | 1347705 B1 | 12/2005 |
| EP | 1688085 A1 | 8/2006 |
| EP | 1839694 A1 | 10/2007 |
| GB | 2218831 A | 11/1989 |
| WO | 94/08647 A1 | 4/1994 |
| WO | 95/24229 A2 | 9/1995 |
| WO | 95/31233 A1 | 11/1995 |
| WO | 9528878 A1 | 11/1995 |
| WO | 96/08281 A1 | 3/1996 |
| WO | 96/14100 A1 | 5/1996 |
| WO | 96/20745 A1 | 7/1996 |
| WO | 96/36389 A1 | 11/1996 |
| WO | 97/21456 A1 | 6/1997 |
| WO | 97/40482 A1 | 10/1997 |
| WO | 98/14234 A1 | 4/1998 |
| WO | 9817336 A1 | 4/1998 |
| WO | 98/20439 A1 | 5/1998 |
| WO | 98/24358 A2 | 6/1998 |
| WO | 98/42407 A1 | 10/1998 |
| WO | 98/49659 A2 | 11/1998 |
| WO | 98/58693 A1 | 12/1998 |
| WO | 98/59487 A1 | 12/1998 |
| WO | 99/08183 A1 | 2/1999 |
| WO | 99/10801 A1 | 3/1999 |
| WO | 99/18532 A1 | 4/1999 |
| WO | 99/22236 A1 | 5/1999 |
| WO | 99/44655 A2 | 9/1999 |
| WO | 99/59663 A1 | 11/1999 |
| WO | 0010628 A2 | 3/2000 |
| WO | 00/28217 A1 | 5/2000 |
| WO | 00/69493 A1 | 11/2000 |
| WO | 01/00261 A1 | 1/2001 |
| WO | 01/61616 A3 | 8/2001 |
| WO | 01/70304 A1 | 9/2001 |
| WO | 02/04047 A2 | 1/2002 |
| WO | 02/49509 A2 | 6/2002 |
| WO | 02/053220 A2 | 7/2002 |
| WO | 02/056945 A2 | 7/2002 |
| WO | 02/070049 A1 | 9/2002 |
| WO | 02083209 A1 | 10/2002 |
| WO | 03/053498 A2 | 7/2003 |
| WO | 03/059422 A1 | 7/2003 |
| WO | 03/063932 A2 | 8/2003 |
| WO | 03/071930 A2 | 9/2003 |
| WO | 03/090838 A1 | 11/2003 |
| WO | 03/094075 A1 | 11/2003 |
| WO | 2004/007133 A1 | 1/2004 |
| WO | 2004/008956 A2 | 1/2004 |
| WO | 2004/009160 A1 | 1/2004 |
| WO | 2004-028596 A1 | 4/2004 |
| WO | 2004/058327 A2 | 7/2004 |
| WO | 2004/069095 A2 | 8/2004 |
| WO | 2004/070548 A2 | 8/2004 |
| WO | 2004/070557 A2 | 8/2004 |
| WO | 2004/070994 A2 | 8/2004 |
| WO | 2004/070995 A2 | 8/2004 |
| WO | 2004/098390 A2 | 11/2004 |
| WO | 2005/000378 A2 | 1/2005 |
| WO | 2005/010796 A2 | 2/2005 |
| WO | 2005/016411 A2 | 2/2005 |
| WO | 2005/019766 A2 | 3/2005 |
| WO | 2005/019987 A2 | 3/2005 |
| WO | 2005/039671 A2 | 5/2005 |
| WO | 2005/094920 A1 | 10/2005 |
| WO | 2005/101279 A2 | 10/2005 |
| WO | 2005-102416 A1 | 11/2005 |
| WO | 2005/112899 A2 | 12/2005 |
| WO | 2005/121938 A2 | 12/2005 |
| WO | 2006/001929 A1 | 1/2006 |
| WO | 2006/023147 A1 | 3/2006 |
| WO | 2006/032652 A1 | 3/2006 |
| WO | 2006/081975 A1 | 8/2006 |
| WO | 2006/083831 A1 | 8/2006 |
| WO | 2006/097453 A1 | 9/2006 |
| WO | 2006/108809 A1 | 10/2006 |
| WO | 2007016145 A1 | 2/2007 |

OTHER PUBLICATIONS

International Search Report with Written Opinion, dated Mar. 31, 2010, in international patent application No. PCT/US09/093169, 23 pgs.
International Search Report and Written Opinion From Corresponding International Application No. PCT/US2007/003490, dated Nov. 28, 2007 (20 pages).
International Search Report and Written Opinion From Corresponding International Application No. PCT/US2007/003567, dated Oct. 17, 2007 (18 pages).
International Search Report and Written Opinion From Corresponding International Application No. PCT/US2007/003587, Nov. 12, 2007 (18 pages).
International Search Report and Written Opinion From Corresponding International Application No. PCT/US2007/003634, Oct. 2, 2007 (18 pages).
Conical fittings with a 6% (Luer) taper for syringes, needles and certain other medical equipment—Lock fittings, British Standard, BS EN 1707 : 1997 (20 pages).
Conical fittings with a 6% (Luer) taper for syringes, needles and certain other medical equipment, Part 1. General requirements, British Standard, BS EN 20594-1 : 1994 ISO 594-1 : 1986 (17 pages).
International Preliminary Report on Patentability From Corresponding International Application No. PCT/US2007/003567, dated Aug. 21, 2008 (11 pages).
Extended European Search Report From European Application No. 09075460.7, dated Mar. 5, 2010 (14 pages).
Office Action from Japanese Appln. No. 2002-591067 dated Jun. 10, 2008 (4 pages).
Non-final Office Action from corresponding U.S. Appl. No. 12/249,891, dated Nov. 18, 2009 (15 pages).

* cited by examiner

PUMP ASSEMBLY WITH A REMOVABLE COVER ASSEMBLY

TECHNICAL FIELD

This disclosure relates to infusion pump assemblies and, more particularly, to infusion pump assemblies that include serviceable battery assemblies.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

SUMMARY OF DISCLOSURE

In a first implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. A combination of the removable cover assembly and at least a portion of the enclosure assembly defines a power supply cavity configured to prevent a removable power supply assembly from being reverse-polarity electrically coupled to the processing logic.

One or more of the following features may be included. The removable cover assembly may be configured to allow access to the power supply cavity and effectuate removable insertion of the removable power supply assembly into the power supply cavity. The removable power supply assembly may include a battery.

The removable cover assembly may include a sealing assembly for releasably engaging at least a portion of the enclosure assembly and forming an essentially water-tight seal between the removable cover assembly and the enclosure assembly. The sealing assembly may include an o-ring assembly. The removable cover assembly may include a conductor assembly configured to electrically couple the removable cover assembly with an interior wall of the power supply cavity.

The removable cover assembly may include a first twist lock assembly. The enclosure assembly may include a second twist lock assembly configured to releasably engage the first twist lock assembly and effectuate the releasable engagement of the removable cover assembly and the enclosure assembly.

In another implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. The removable cover assembly includes a sealing assembly for releasably engaging at least a portion of the enclosure assembly and forming an essentially water-tight seal between the removable cover assembly and the enclosure assembly. A combination of the removable cover assembly and at least a portion of the enclosure assembly define a power supply cavity configured to allow removable insertion of a removable power supply assembly.

One or more of the following features may be included. The removable cover assembly may be configured to allow access to the power supply cavity and effectuate removable insertion of the removable power supply assembly into the power supply cavity. The removable power supply assembly may include a battery. The sealing assembly may include an o-ring assembly.

The removable cover assembly may include a conductor assembly configured to electrically couple the removable cover assembly with an interior wall of the power supply cavity. The removable cover assembly may include a first twist lock assembly. The enclosure assembly may include a second twist lock assembly configured to releasably engage the first twist lock assembly and effectuate the releasable engagement of the removable cover assembly and the enclosure assembly.

In another implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly, which is configured to releasably engage the enclosure assembly, includes a first twist lock assembly. A combination of the removable cover assembly and at least a portion of the enclosure assembly define a power supply cavity configured to allow removable insertion of a removable power supply assembly. The enclosure assembly includes a second twist lock assembly configured to releasably engage the first twist lock assembly and effectuate the releasable engagement of the removable cover assembly and the enclosure assembly.

One or more of the following features may be included. The removable cover assembly may be configured to allow access to the power supply cavity and effectuate removable insertion of the removable power supply assembly into the power supply cavity. The removable power supply assembly may include a battery. The removable cover assembly may include a conductor assembly configured to electrically couple the removable cover assembly with an interior wall of the power supply cavity.

In another implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. A combination of the removable cover assembly and at least a portion of the enclosure assembly defines a power supply cavity configured to allow removable insertion of the removable power supply assembly. The removable cover assembly includes a conductor assembly configured to electrically couple the removable cover assembly with an interior wall of the power supply cavity.

One or more of the following features may be included. The removable cover assembly may be configured to allow access to the power supply cavity and effectuate removable insertion of the removable power supply assembly into the power supply cavity. The removable power supply assembly may include a battery.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
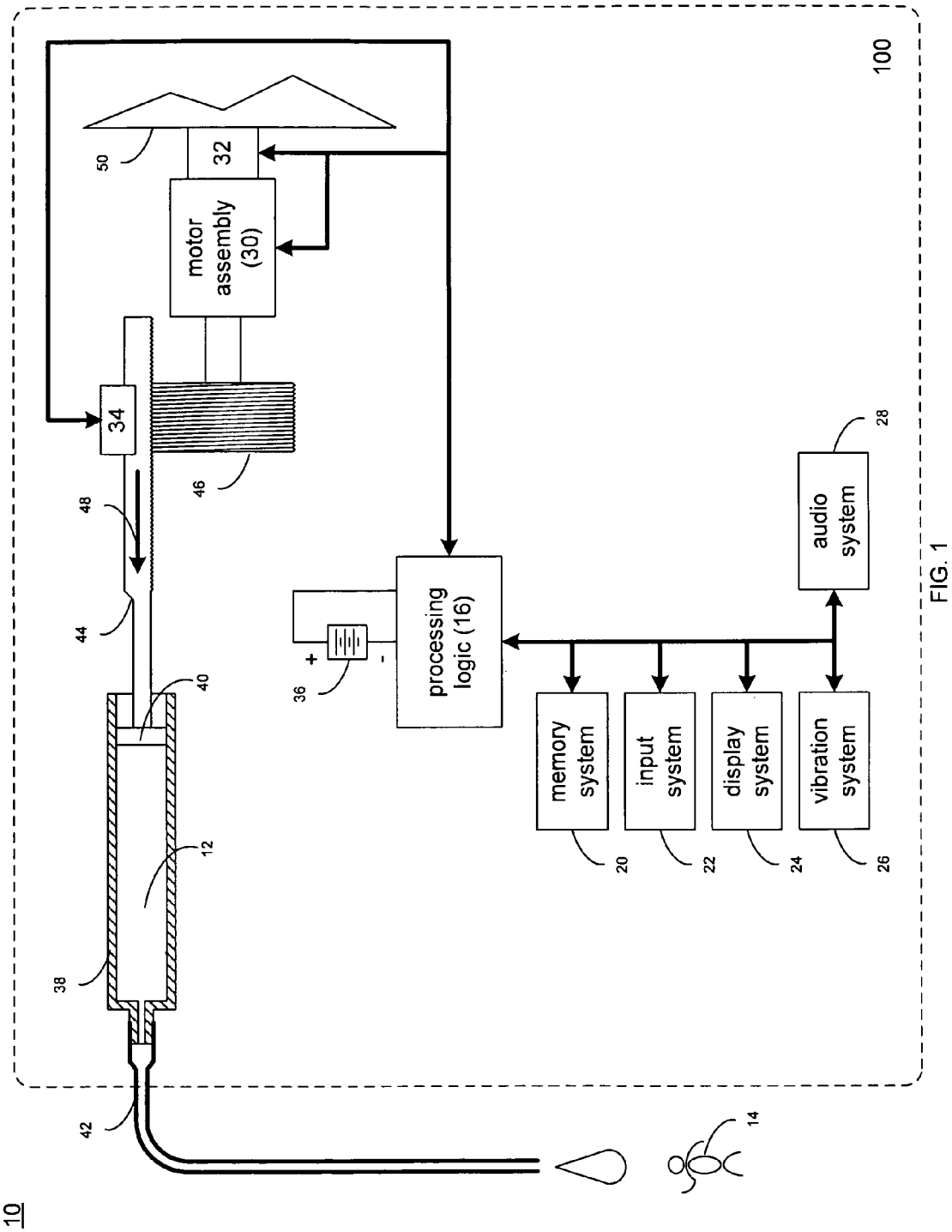
FIG. 1 is a diagrammatic view of an infusion pump assembly.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs, and any other therapeutic fluids.

Infusion pump assembly 10 may include processing logic 16 that executes one or more processes that may be required for infusion pump assembly 10 to operate properly. Processing logic 16 may include one or more microprocessors (not shown), one or more input/output controllers (not shown), and cache memory devices (not shown). One or more data buses and/or memory buses may be used to interconnect processing logic 16 with one or more subsystems.

Examples of the subsystems interconnected with processing logic 16 may include but are not limited to memory system 20, input system 22, display system 24, vibration system 26, audio system 28, motor assembly 30, force sensor 32, and displacement detection device 34. Infusion pump assembly 10 may include removable power supply assembly 36 (e.g. a battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

Infusion pump assembly 10 may include reservoir assembly 38 configured to contain infusible fluid 12. In some embodiments, the reservoir assembly 38 may be a reservoir assembly similar to that described in U.S. Patent Application Publication No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. In this particular embodiment, the combination of motor assembly 30, plunger assembly 40, partial nut assembly 44, and lead screw assembly 46 may form a pump assembly that effectuates the dispensing of infusible fluid 12 contained within reservoir assembly 38. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578 issued Dec. 11, 2007 which is herein incorporated by reference in its entirely.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide the appropriate drive signals to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate three-thousand revolutions for each revolution of lead screw assembly 46, thus increasing the torque and resolution of motor assembly 30 by a factor of three-thousand.

As discussed above, infusion pump assembly 10 may be configured to deliver infusible fluid 12 to user 14. Infusible fluid 12 may be delivered to user 14 via one or more different infusion event types. For example, infusion pump assembly 10 may deliver infusible fluid 12 via a sequential, multi-part, infusion event (that may include a plurality of discrete infusion events) and/or a one-time infusion event.

Examples of such a sequential, multi-part, infusion event may include but are not limited to a basal infusion event and an extended-bolus infusion event. As is known in the art, a basal infusion event refers to the repeated injection of small (e.g. 0.05 unit) quantities of infusible fluid 12 at a predefined interval (e.g. every three minutes) that is repeated. Further, the basal infusion rates may be pre-programmed and may include specified rates for pre-programmed time-frames, e.g., a rate of 0.50 units per hour from 6 am-3 pm; a rate of 0.40 units per hour from 3 pm-10 pm; and a rate of 0.35 units per hour from 10 pm-6 am. However, similarly, the basal rate may be 0.025 units per hour, and may not change according to pre-programmed time-frames. The basal rates may be repeated regularly/daily until otherwise changed.

Further and as is known in the art, an extended-bolus infusion event refers to the repeated injection of small (e.g. 0.025 unit) quantities of infusible fluid 12 at a predefined interval (e.g. every three minutes) that is repeated for a defined number of intervals (e.g., three intervals) or for a defined period of time (e.g., one hour). An extended-bolus infusion event may occur simultaneously with a basal infusion event.

In contrast, as is known in the art, a normal bolus infusion event refers to a one-time infusion of infusible fluid 12. The volume of the infusible fluid 12 delivered in a bolus infusion event may be requested, and infusion pump assembly 10 may deliver the requested volume of infusible fluid 12 for the bolus infusion event at a predetermined rate (e.g., as quickly as the infusion pump assembly can deliver). However, the infusion pump assembly may deliver a normal bolus at a slower rate where the normal bolus volume is greater than a pre-programmed threshhold.

Referring also to FIGS. 2, 2L, 2R & 3, the above-described components of infusion pump assembly 10 may be included within enclosure assembly 100. Enclosure assembly 100 may be configured so that display system 24 is visible by user 14 through enclosure assembly 100. One or more switch assemblies/input devices 102, 104, 106 (included within input system 22) may be positioned about various portions of enclosure assembly 100. Enclosure assembly 100 may include infusion port assembly 108 to which cannula assembly 42 may be releasably coupled. A combination of removable cover assembly 110 and a portion of enclosure assembly 100 may define power supply cavity 112 (shown in phantom on FIG. 2).

Figure 4:
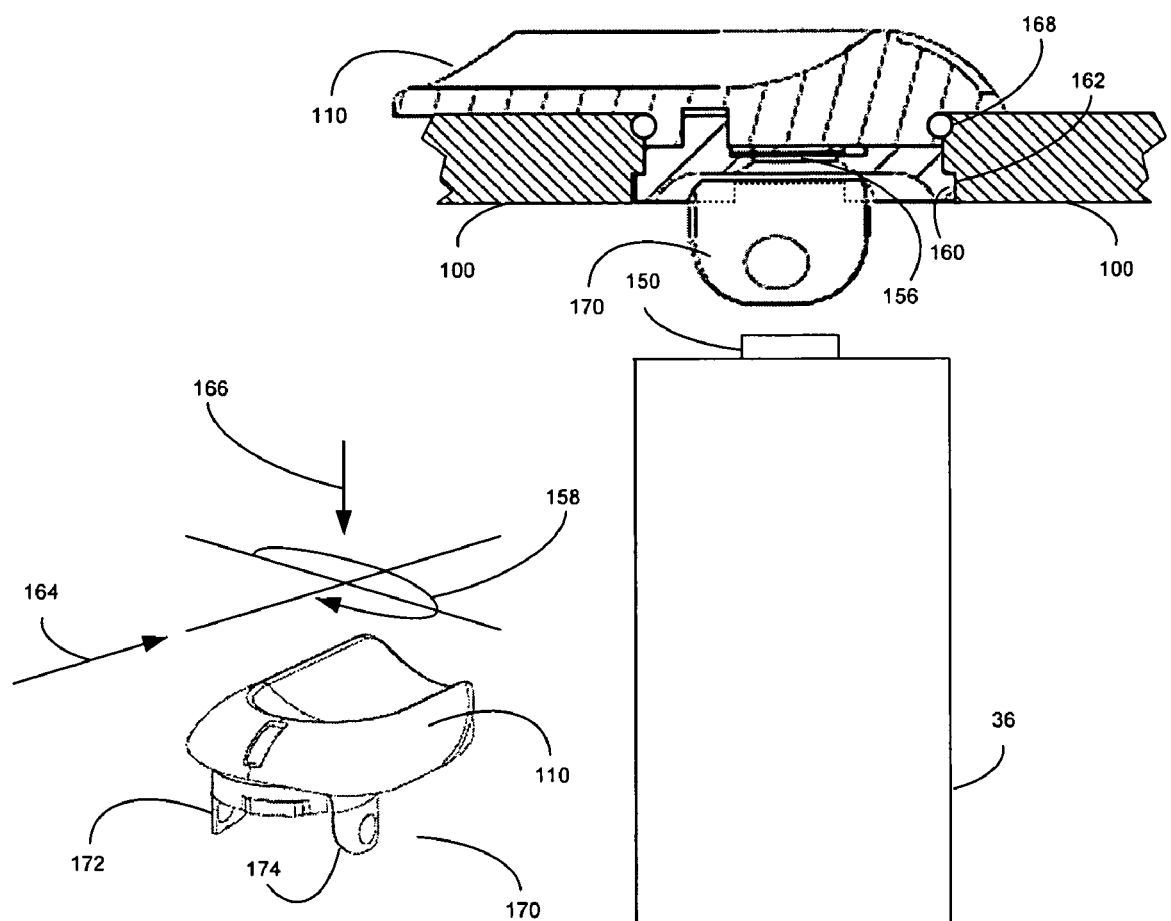
FIG. 4 is an isometric view of a removable cover assembly for use with the infusion pump assembly of FIG. 2.
Figure 5:
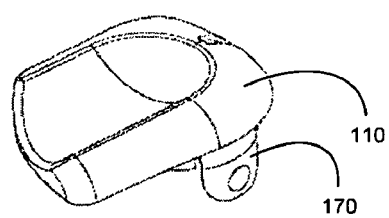
FIG. 5 is an alternative isometric view of the removable cover assembly of FIG. 4.
Figure 6:
FIG. 6 is a cross-sectional view of the removable cover assembly of FIG. 4.

Referring also to FIGS. 4-6, power supply cavity 112 (which is formed by a combination of removable cover assembly 110 and a portion of enclosure assembly 100) may be configured to releasably receive removable power supply assembly 36. Additionally, power supply cavity 112 may be configured to prevent removable power supply assembly 36 from being reverse-polarity electrically coupled to processing logic 16. For example, power supply cavity 112 may be configured to prevent positive terminal 150 of removable power supply assembly 36 from being electrically coupled to negative terminal 152 of power supply cavity 112 and/or negative terminal 154 of removable power supply 36 from being electrically coupled to positive terminal 156 of power supply cavity 112).

Configuring power supply cavity 112 to prevent removable power supply 36 from being reverse-polarity electrically coupled to processing logic 16 may provide various benefits. For example, the configuration may prevent the loss of power from the removable power supply assembly 36 (e.g., discharge of the battery) where the removable power supply assembly 36 has been inserted incorrectly. In addition to functioning to not waste power, this configuration may also be a safety feature to infusion pump assembly 10. Infusion pump assembly 10 may rely on power for functionality. A user may rely on infusion pump assembly 10 to provide life-sustaining therapy, for example, by delivering insulin. Thus, preventing removable power supply assembly 36 from being reverse-polarity electrically coupled to processing logic 16 (e.g., as a result of user 14 having mistakenly inserted removable power supply assembly 36 incorrectly), preventing removable power supply 36 from being reverse-polarity electrically coupled to processing logic 16 may allow infusion pump assembly 10 to function for a longer time than if the incorrectly installed removable power supply assembly 36 had been able to be reverse-polarity electrically coupled to processing logic 16.

Removable cover assembly 110 may be configured to allow access to power supply cavity 112 and effectuate the installation/replacement/removal of removable power supply assembly 36. As discussed above, an example of removable power supply assembly 36 may include but is not limited to a battery. In some embodiments, the battery may include, but is not limited to, an A, AA, AAA or AAAA battery, and the battery may be a lithium battery or alkaline battery. The battery may, in some embodiments, be a rechargeable battery.

Removable cover assembly 110 may be configured to rotatably engage enclosure assembly 100 in the direction of arrow 158. For example, removable cover assembly 110 may include first twist lock assembly 160 (e.g., a protruding tab). Enclosure assembly 100 may include a second twist lock assembly 162 (e.g., a slot) configured to releasably engage first twist lock assembly and effectuate the releasable engagement of the removable cover assembly and the enclosure assembly.

While removable cover assembly 110 and enclosure assembly 100 is described above as including first twist lock assembly 160 and second twist lock assembly 162, this is for illustrative purposes only and is not intended to be a limitation of this disclosure, as other configurations are possible and are considered to be within the scope of this disclosure. For example, one or more thread assemblies (not shown) may be utilized to effectuate the above-described rotatable engagement.

Further, while removable cover assembly 110 is described above as being configured to rotatably engage enclosure assembly 100, this is for illustrative purposes only and is not intended to be a limitation of this disclosure, as other configurations are possible. For example, removable cover assembly 110 may be configured to slidably engage enclosure assembly 100 (in the direction of arrow 164) using a slide assembly (not shown). Alternatively, removable cover assembly 110 may be configured to be pressed into enclosure assembly 100 in the direction of arrow 166.

Removable cover assembly 110 may include sealing assembly 168 (e.g., an o-ring assembly) that is configured to releasably engage at least a portion of enclosure assembly 100 to form an essentially water-tight seal between removable cover assembly 110 and enclosure assembly 100.

In an embodiment in which sealing assembly 168 includes an o-ring assembly included within removable cover assembly 110, the o-ring assembly may be sized to effectuate a watertight (or essentially watertight) seal with a corresponding surface of enclosure assembly 100.

Alternatively, in an embodiment in which sealing assembly 168 includes an o-ring assembly included within enclosure assembly 100, the o-ring assembly may be sized to effectuate a watertight (or essentially watertight) seal with a corresponding surface of removable cover assembly 110.

Removable cover assembly 110 may include conductor assembly 170 for electrically coupling positive terminal 156 of removable cover assembly 110 with interior wall 114 of power supply cavity 112. For example, conductor assembly 170 may include a plurality of tabs (e.g., tabs 172, 174) that may be electrically coupled to positive terminal 156 of removable cover assembly 110. Tabs 172, 174 may be configured so that when removable cover assembly 110 releasably engages enclosure assembly 100, tabs 172, 174 may make electrical contact with interior wall 114 of power supply cavity 112. Interior wall 114 of power supply cavity 112 may then be electrically coupled to the various components within infusion pump assembly 10 that require electrical power, examples of which may include but are not limited to processing logic 16.

Figure 7:
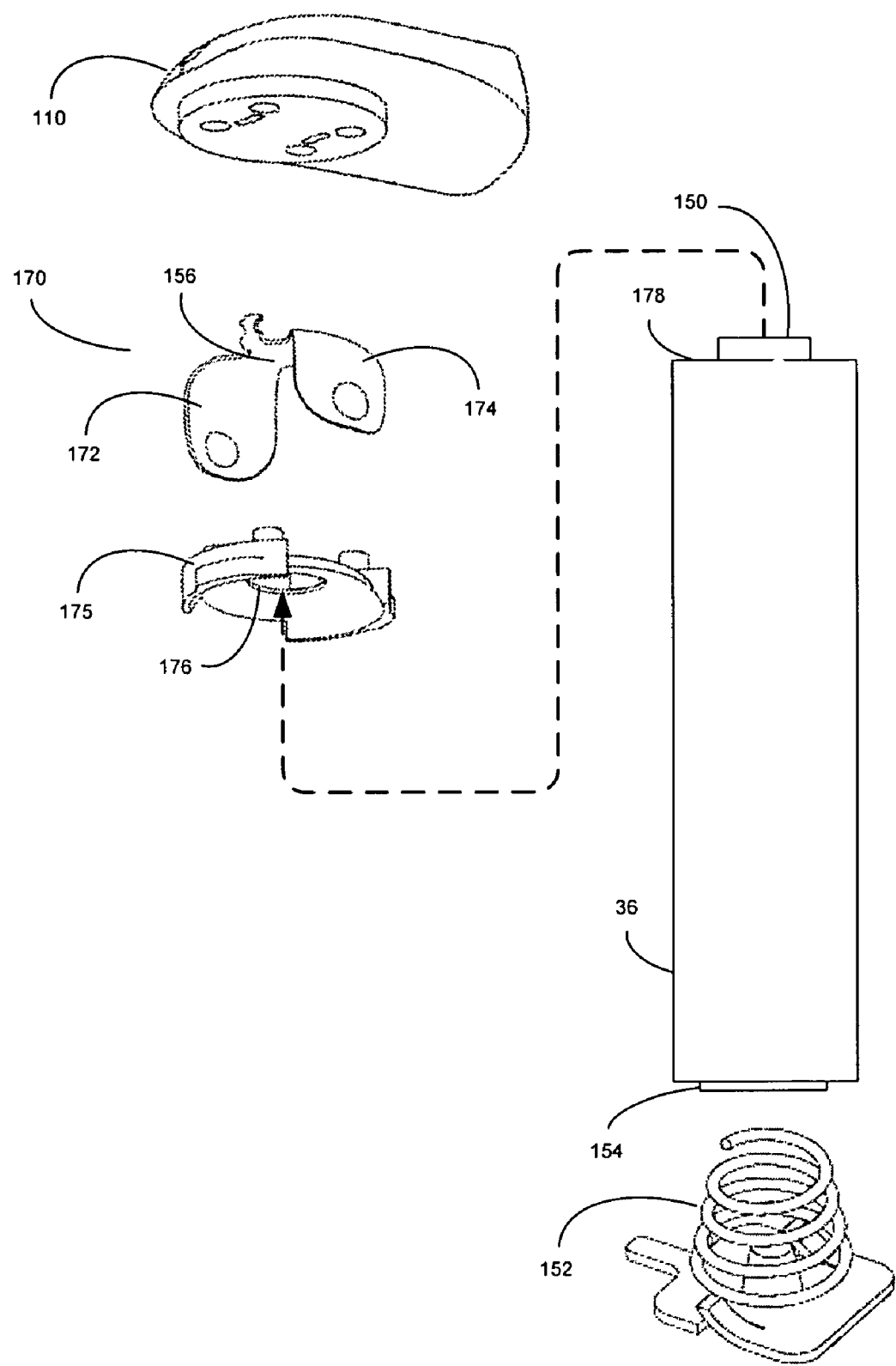
FIG. 7 is an alternative isometric view of the removable cover assembly of FIG. 4.
Figure 8A:
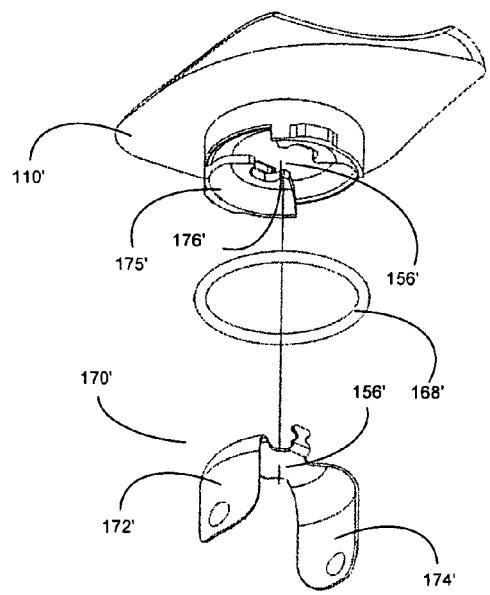
FIG. 8A-8D are isometric views of an alternative embodiment of the removable cover assembly of FIG. 4.
Figure 8B:
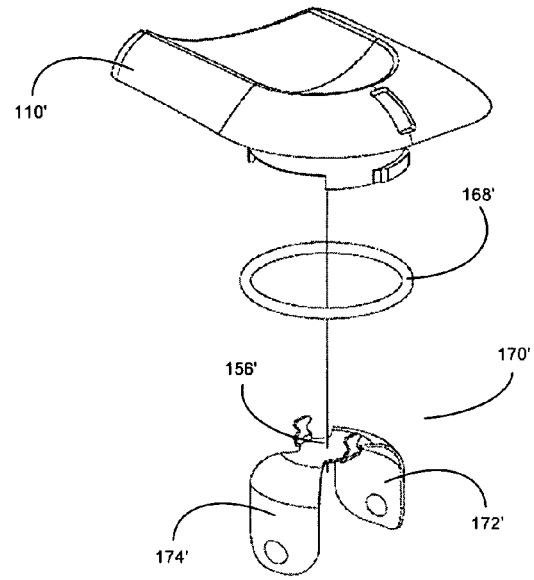
Figure 8C:
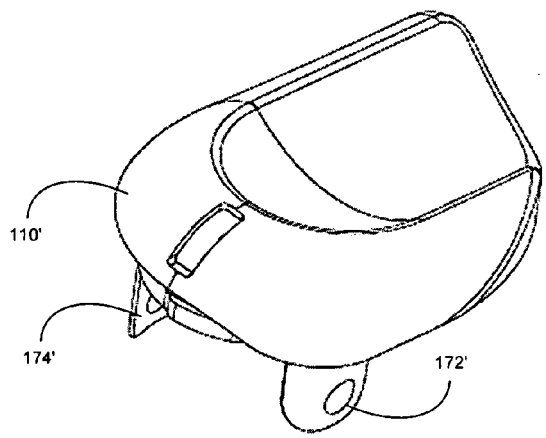
Figure 8D:
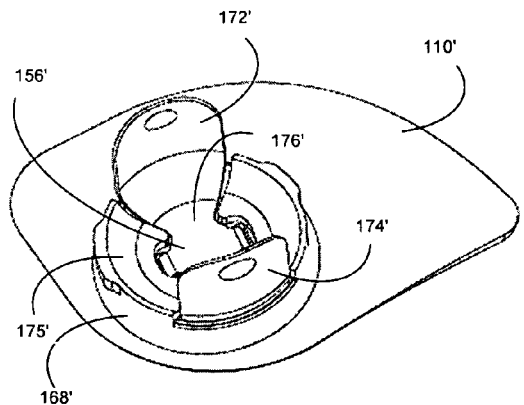

As discussed above, the combination of removable cover assembly 110 and a portion of enclosure assembly 100 may be configured to prevent removable power supply assembly 36 from being reverse-polarity electrically coupled to processing logic 16. Referring also to FIG. 7, one or more of negative terminal 152 and positive terminal 156 may be configured so that the above-described reverse polarity situation cannot occur. For example, removable cover assembly 110 may include insulator assembly 175 that includes recess 176 that is sized to receive positive terminal 150 of removable power supply assembly 36 and enable electrical contact with positive terminal 156 of removable cover assembly 110. Insulator assembly 175 may be constructed of an insulating material, for example, but limited to, plastic, for example, but not limited to, PVC plastic or bakelite. Further, recess 176 may be sized so that negative terminal 154 of removable power supply assembly 36 cannot make electrical contact with positive terminal 156 (and may only make contact with insulator 176), thus preventing removable power supply assembly 36 from being electrically coupled to processing logic 16 in a reverse-polarity configuration.

Referring also to FIGS. 8A-8D, there is shown an alternative-embodiment removable cover assembly 110'. Removable cover assembly 110' may include sealing assembly 168' (e.g., an o-ring assembly) that is configured to releasably engage at least a portion of enclosure assembly 100 to form an essentially water-tight seal between removable cover assembly 110' and enclosure assembly 100.

Figure 2R:
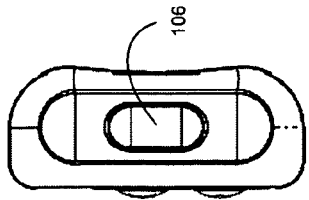
FIG. 2R is a right-side view of the infusion pump assembly of FIG. 2.
Figure 2:
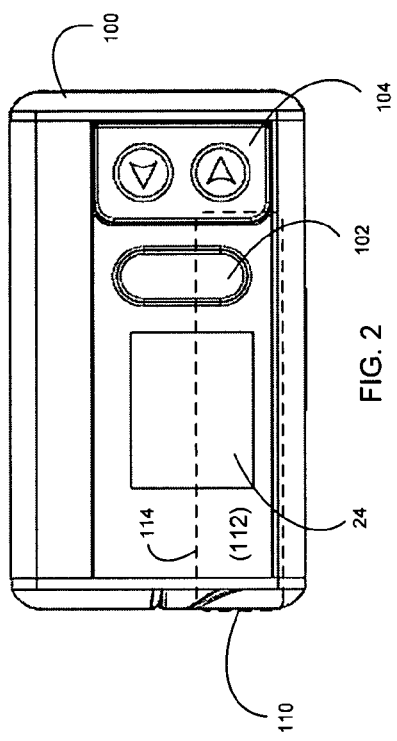
FIG. 2 is a front view of the infusion pump assembly of FIG. 1.
Figure 2L:
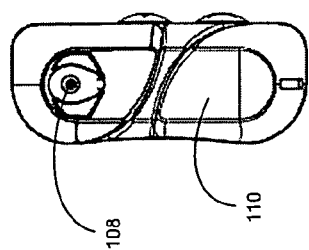
FIG. 2L is a left-side view of the infusion pump assembly of FIG. 2.
Figure 3:
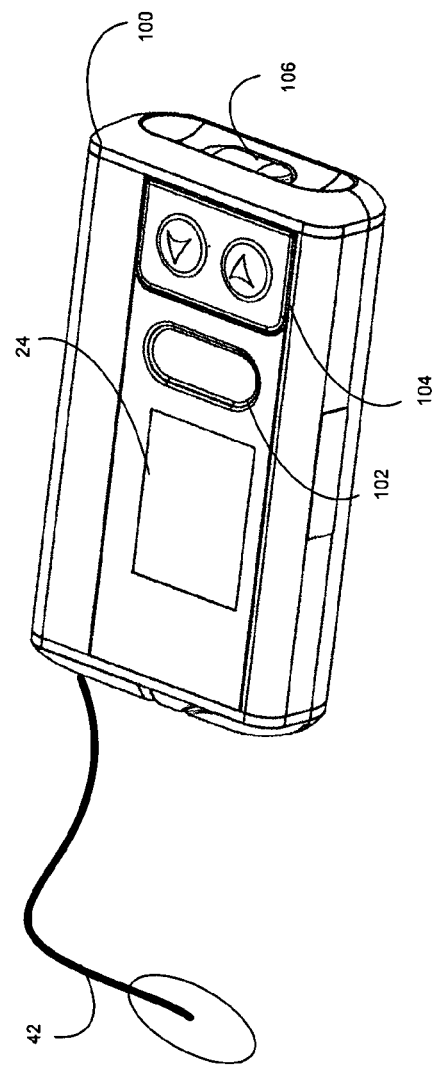
FIG. 3 is an isometric view of the infusion pump assembly of FIG. 2.

Removable cover assembly 110' may include conductor assembly 170' for electrically coupling positive terminal 156' of removable cover assembly 110' with interior wall 114 (FIG. 2) of power supply cavity 112 (FIG. 2). For example, conductor assembly 170' may include a plurality of tabs (e.g., tabs 172', 174') that may be electrically coupled to positive terminal 156' of removable cover assembly 110'. Tabs 172', 174' may be configured so that when removable cover assembly 110' releasably engages enclosure assembly 100 (FIG. 2), tabs 172', 174' may make electrical contact with interior wall 114 of power supply cavity 112. Interior wall 114 of power supply cavity 112 may then be electrically coupled to the various components within infusion pump assembly 10 that require electrical power, examples of which may include but are not limited to processing logic 16.

As discussed above, the combination of removable cover assembly 110' and a portion of enclosure assembly 100 may be configured to prevent removable power supply assembly 36 from being reverse-polarity electrically coupled to processing logic 16. For example, removable cover assembly 110' may include insulator assembly 175' that defines recess 176' that is sized to receive positive terminal 150 (FIGS. 6-7) of removable power supply assembly 36 (FIGS. 6-7) and enable electrical contact with positive terminal 156' of removable cover assembly 110'. Insulator assembly 175', which may be constructed of an insulating material (which in some embodiments may include, but is not limited to plastic, which may include, but is not limited to, PVC plastic or bakelite), may be molded into and/or a portion of removable cover assembly 110'. Further, recess 176' may be sized so that negative terminal 154 (FIGS. 6-7) of removable power supply assembly 36 cannot make electrical contact with positive terminal 156' (and may only make electrical contact with insulator 176', thus preventing removable power supply assembly 36 from being electrically coupled to processing logic 16 in a reverse-polarity configuration.

While power supply cavity 112 is described above as having positive terminal 156 positioned proximate removable cover assembly 110, this is for illustrative purposes only and is not intended to be a limitation of this disclosure, as other configurations are possible and are considered to be within the scope of this disclosure. For example, negative terminal 152 may be positioned proximate removable cover assembly 110.

A number of implementations have been described. Nevertheless, it will be understood that various modifications may be made. Accordingly, other implementations are within the scope of the following claims.

What is claimed is:

1. An infusion pump assembly comprising:
   an enclosure assembly;
   a reservoir assembly positioned at least partially within the enclosure assembly and configured to contain an infusible fluid;
   a pump assembly positioned at least partially within the enclosure assembly and configured to effectuate the dispensing of the infusible fluid contained within the reservoir assembly;
   processing logic positioned at least partially within the enclosure assembly and configured to control the pump assembly; and
   a removable cover assembly configured to releasably engage the enclosure assembly;

wherein a combination of the removable cover assembly and at least a portion of the enclosure assembly define a power supply cavity, the combination preventing a removable power supply assembly within the power supply cavity from being reverse-polarity electrically coupled to the processing logic; and wherein:
the removable cover assembly includes a first twist lock assembly; and
the enclosure assembly includes a second twist lock assembly configured to releasably engage the first twist lock assembly and effectuate the releasable engagement of the removable cover assembly and the enclosure assembly.

2. The infusion pump assembly of claim 1 wherein the removable cover assembly covers an access opening when engaging the enclosure assembly that allows access to the power supply cavity and effectuates removable insertion of the removable power supply assembly into the power supply cavity.

3. The infusion pump assembly of claim 1 wherein the removable power supply assembly includes a battery.

4. The infusion pump assembly of claim 1 wherein the removable cover assembly includes:
a sealing assembly for releasably engaging at least a portion of the enclosure assembly and forming an essentially water-tight seal between the removable cover assembly and the enclosure assembly.

5. The infusion pump assembly of claim 4 wherein the sealing assembly includes an o-ring assembly.

6. The infusion pump assembly of claim 1 wherein the removable cover assembly includes:
a conductor assembly configured to electrically couple the removable cover assembly with an interior wall of the power supply cavity.

7. An infusion pump assembly comprising:
an enclosure assembly;
a reservoir assembly positioned at least partially within the enclosure assembly and configured to contain an infusible fluid;
a pump assembly positioned at least partially within the enclosure assembly and configured to effectuate the dispensing of the infusible fluid contained within the reservoir assembly;
processing logic positioned at least partially within the enclosure assembly and configured to control the pump assembly; and
a removable cover assembly configured to releasably engage the enclosure assembly, the removable cover assembly including a sealing assembly for releasably engaging at least a portion of the enclosure assembly and forming an essentially water-tight seal between the removable cover assembly and the enclosure assembly;
wherein a combination of the removable cover assembly and at least a portion of the enclosure assembly define a power supply cavity configured to allow removable insertion of a removable power supply assembly, the power supply cavity having an access opening that is covered by the removable cover assembly when engaged with the enclosure assembly;
wherein the sealing assembly substantially surrounds the access opening; and wherein:
the removable cover assembly includes a first twist lock assembly; and
the enclosure assembly includes a second twist lock assembly configured to releasably engage the first twist lock assembly and effectuate the releasable engagement of the removable cover assembly and the enclosure assembly.

8. The infusion pump assembly of claim 7 wherein the removable cover assembly is configured to allow access to the power supply cavity and effectuate removable insertion of the removable power supply assembly into the power supply cavity.

9. The infusion pump assembly of claim 7 wherein the removable power supply assembly includes a battery.

10. The infusion pump assembly of claim 7 wherein the sealing assembly includes an o-ring assembly.

11. The infusion pump assembly of claim 7 wherein the removable cover assembly includes:
a conductor assembly configured to electrically couple the removable cover assembly with an interior wall of the power supply cavity.

12. An infusion pump assembly comprising:
an enclosure assembly;
a reservoir assembly positioned at least partially within the enclosure assembly and configured to contain an infusible fluid;
a pump assembly positioned at least partially within the enclosure assembly and configured to effectuate the dispensing of the infusible fluid contained within the reservoir assembly;
processing logic positioned at least partially within the enclosure assembly and configured to control the pump assembly; and
a removable cover assembly configured to releasably engage the enclosure assembly, the removable cover assembly including a first twist lock assembly having at least one tab;
wherein a combination of the removable cover assembly and at least a portion of the enclosure assembly define a power supply cavity configured to allow removable insertion of a removable power supply assembly; and
wherein the enclosure assembly includes a second twist lock assembly having at least one slot configured to releasably engage the at least one tab of the first twist lock assembly and effectuate the releasable engagement of the removable cover assembly and the enclosure assembly.

13. The infusion pump assembly of claim 12 wherein the removable cover assembly is configured to allow access to the power supply cavity and effectuate removable insertion of the removable power supply assembly into the power supply cavity.

14. The infusion pump assembly of claim 12 wherein the removable power supply assembly includes a battery.

15. The infusion pump assembly of claim 12 wherein the removable cover assembly includes:
a conductor assembly configured to electrically couple the removable cover assembly with an interior wall of the power supply cavity .

* * * * *